(12) United States Patent
Richardson et al.

(10) Patent No.: US 11,474,117 B2
(45) Date of Patent: Oct. 18, 2022

(54) UTILISING FRAGMENTATION IN ANALYSIS OF LIPIDS AND OTHER COMPOUND CLASSES

(71) Applicant: MICROMASS UK LIMITED, Wilmslow (GB)

(72) Inventors: Keith George Richardson, High Peak (GB); Steven Derek Pringle, Darwen (GB)

(73) Assignee: Micromass UK Limited, Wilmslow (GB)

( * ) Notice: Subject to any disclaimer, the term of this patent is extended or adjusted under 35 U.S.C. 154(b) by 651 days.

(21) Appl. No.: 16/471,469

(22) PCT Filed: Dec. 21, 2017

(86) PCT No.: PCT/GB2017/053871
§ 371 (c)(1),
(2) Date: Jun. 19, 2019

(87) PCT Pub. No.: WO2018/115894
PCT Pub. Date: Jun. 28, 2018

(65) Prior Publication Data
US 2020/0278360 A1 Sep. 3, 2020

(30) Foreign Application Priority Data

Dec. 22, 2016 (GB) ..................... 1621927

(51) Int. Cl.
*G01N 33/92* (2006.01)
*G01N 27/62* (2021.01)
(Continued)

(52) U.S. Cl.
CPC .......... *G01N 33/92* (2013.01); *G01N 27/622* (2013.01); *H01J 49/0031* (2013.01);
(Continued)

(58) Field of Classification Search
CPC ...... G01N 27/622; G01N 33/48; G01N 33/68; G01N 33/6848; G01N 33/92;
(Continued)

(56) References Cited

U.S. PATENT DOCUMENTS 8,809,768 B2 * 8/2014 Bateman ............. H01J 49/0027
250/281
9,697,996 B2 * 7/2017 Brown ................ H01J 49/0045
(Continued)

FOREIGN PATENT DOCUMENTS

DE 10 2016 110474 A1 12/2016
GB 2409764 A 7/2005
(Continued)

OTHER PUBLICATIONS

Combined Search and Examination Report under Sections 17 and 18(3), for Application No. GB1721661.5, dated Jun. 21, 2018, 8 pages.

(Continued)

*Primary Examiner* — Maureen Wallenhorst
(74) *Attorney, Agent, or Firm* — Goodwin Procter LLP

(57) ABSTRACT

A method of mass and/or ion mobility spectrometry is disclosed that includes ionising analyte from a sample so as to generate a plurality of ions, separating precursor ions from first fragment and/or other ions of the plurality of ions, fragmenting or reacting at least some of the precursor ions using a fragmentation, reaction or collision device so as to generate second fragment ions, and then analysing at least some ions that emerge from the fragmentation, reaction or collision device. The sample is classified and/or identified based on the analysis of the second fragment ions.

18 Claims, 7 Drawing Sheets

(51) Int. Cl.
  *G01N 33/68* (2006.01)
  *H01J 49/00* (2006.01)
  *G01N 27/622* (2021.01)

(52) U.S. Cl.
  CPC ...... *H01J 49/0036* (2013.01); *H01J 49/0045* (2013.01); *G01N 33/6848* (2013.01); *Y10T 436/24* (2015.01)

(58) Field of Classification Search
  CPC ............... H01J 49/0031; H01J 49/0036; H01J 49/0045; Y10T 436/24
  USPC .................. 436/63, 71, 86, 94, 139, 173
  See application file for complete search history.

(56) References Cited

U.S. PATENT DOCUMENTS

| | | | |
|---|---|---|---|
| 9,881,778 B2* | 1/2018 | Brown | H01J 49/004 |
| 2002/0070338 A1 | 6/2002 | Loboda | |
| 2008/0296486 A1 | 12/2008 | Blanksby et al. | |
| 2016/0005581 A1 | 1/2016 | Graichen et al. | |
| 2016/0349233 A1* | 12/2016 | Astarita | H01J 49/005 |
| 2017/0003268 A1* | 1/2017 | Astarita | H01J 49/0045 |

FOREIGN PATENT DOCUMENTS

| | | | |
|---|---|---|---|
| GB | 2443952 | A | 5/2008 |
| WO | 2014/076556 | A1 | 5/2014 |
| WO | 2014076556 | A1 | 5/2014 |
| WO | 2015/071650 | * | 5/2015 |
| WO | 2015/159063 | A1 | 10/2015 |
| WO | 2015/189749 | A1 | 12/2015 |
| WO | 2015189749 | A1 | 12/2015 |
| WO | 2016/090471 | A1 | 6/2016 |
| WO | 2016090471 | A1 | 6/2016 |
| WO | 2016/142674 | A1 | 9/2016 |
| WO | 2016142674 | A1 | 9/2016 |

OTHER PUBLICATIONS

Author unknown, "Tandem Mass Spectrometry", Wikipedia.com [online] retrieved on Jul. 13, 2020. Retrieved from Internet URL: https://en.wikipedia.org/w/lindex.phptitle=Tandem_mass_spectrometry oldid=732352170, 13 pages.
Damen, C. W. N., et al., "Enhanced lipid isomer separation in human plasma using reversed-phase UPLC with ionmobility/high-resolution MS detection," Journal of Lipid Research, 55(8):1772-1783, (2014).
Guo, Z., and He, L., "A binary matrix for background suppression in MALDI-MS of small molecules", Analytical and Bioanalytical Chemistry, 387:193901944 (2007). ABSTRACT.
Xu, Y-F, et al., "Avoiding Misannotation of In-Source Fragmentation Products as Cellular Metabolites in Liquid Chromatography-Mass Spectrometry-Based Metabolomics" Analytical Chemistry, 87(4):2273-2281 (2015).
Barnett, D.A., et al., "Tandem mass spectra of tryptic peptides at signal-to-background ratios approaching unity using electrospray ionization high-field asymmetric waveform ion mobility spectrometry/hybrid quadrupole time-of-flight mass spectrometry" Rapid Comm in Mass Spectrometry 16(7):676-680 (2002). ABSTRACT.
Examination Report under Section 18(3) for Application No. GB1721661.5, dated Nov. 11, 2020, 4 pages.
Search Report for United Kingdom Patent Application No. GB1621927.1, dated Jun. 8, 2017.
Combined Search and Examination Report for United Kingdom Patent Application No. GB1721661.5, dated Jun. 21, 2018.
International Search Report and Written Opinion for Internation Application No. PCT/GB2017/053871, dated Mar. 26, 2018.
Damen, C. W. N., et al., "Enhanced lipid isomer separation in human plasma using reversed-phase UPLC with ion-mobility/high-resolution MS detection," Journal of Lipid Research, 55(8):1772-1783, Jun. 2, 2014.
Wikipedia, 2016, "Tandem mass spectrometry", Wikipedia.com, https://en.wikipedia.org/w/index.php?title=Tandem_mass_spectrometry &oldid=732352170 [accessed Jun. 20, 2018].

* cited by examiner

Fig. 5

| m/z | Ion Description |
|---|---|
| 674.4766 | Precursor ion [M-H]- |
| 464.2783 | Loss of sn2 acyl chain as ketene (RCH=C=O) from [M-H]- |
| 446.2677 | Neutral loss of sn2 RCOOH group from [M-H]- |
| 424.2470 | Loss of sn1 acyl chain as ketene (RCH=C=O) from [M-H]- |
| 406.2364 | Neutral loss of sn1 RCOOH group from [M-H]- |
| 267.2330 | sn1 RCOO- ion |
| 227.2017 | sn2 RCOO- ion |
| 152.9958 | Glycerol-3-phosphate ion with loss of H2O |
| 140.0118 | Ethanolamine phosphate ion |
| 122.0013 | Ethanolamine phosphate ion with loss of H2O |
| 96.9696 | H2PO4- ion (from phosphate) |
| 78.9591 | PO3- ion (from phosphate) |

Fig. 5 (Cont.)

| m/z | Ion Description |
|---|---|
| 674.4766 | Precursor ion [M-H]- |
| 478.2939 | Loss of sn1 acyl chain as ketene (RCH=C=O) from [M-H]- |
| 460.2834 | Neutral loss of sn1 RCOOH group from [M-H]- |
| 410.2313 | Loss of sn2 acyl chain as ketene (RCH=C=O) from [M-H]- |
| 392.2208 | Neutral loss of sn2 RCOOH group from [M-H]- |
| 281.2486 | sn2 RCOO- ion |
| 213.1860 | sn1 RCOO- ion |
| 152.9958 | Glycerol-3-phosphate ion with loss of H2O |
| 140.0118 | Ethanolamine phosphate ion |
| 122.0013 | Ethanolamine phosphate ion with loss of H2O |
| 96.9696 | H2PO4- ion (from phosphate) |
| 78.9591 | PO3- ion (from phosphate) |

UTILISING FRAGMENTATION IN ANALYSIS OF LIPIDS AND OTHER COMPOUND CLASSES

CROSS-REFERENCE TO RELATED APPLICATION

This application claims priority from and the benefit of United Kingdom patent application No. 1621927.1 filed on 22 Dec. 2016. The entire content of this application is incorporated herein by reference.

FIELD OF THE INVENTION

The present invention relates generally to methods of mass and/or ion mobility spectrometry and in particular to their use in methods of classifying and/or identifying samples such as biological or other samples.

BACKGROUND

Rapid Evaporative Ionisation Mass Spectrometry ("REIMS") analysis is becoming accepted as an effective method for direct analysis of a wide range of samples including (among many others) biological samples such as human and animal tissues, food and microbe cultures.

In the REIMS technique, an electric current is used to generate an aerosol from the sample. Some of the resulting aerosol is passed into the source of a mass spectrometer wherein it collides with a heated impact surface. Ions are generated on or near the impact surface and these are transmitted onward through the spectrometer, so as to generate mass spectra that are characteristic of the type of sample being ionised. Models or libraries created using these spectra can be used for identification of the same sample types.

However, the mass spectra can be complex, can contain peaks relating to isobaric species or closely spaced peaks that cannot be resolved, and can suffer from low reproducibility, thereby reducing the performance of classification and/or identification algorithms.

It is desired to provide an improved method of mass and/or ion mobility spectrometry.

SUMMARY

According to an aspect there is provided a method of mass and/or ion mobility spectrometry comprising:

ionising analyte from a sample so as to generate a plurality of ions;

separating precursor ions from first fragment and/or other ions of the plurality of ions;

fragmenting or reacting at least some of the precursor ions using a fragmentation, reaction or collision device so as to generate second fragment ions;

analysing at least some ions that emerge from the fragmentation, reaction or collision device; and classifying and/or identifying the sample based on the analysis of the second fragment ions.

Various embodiments are directed to methods of mass and/or ion mobility spectrometry in which analyte from a sample is ionised so as to generate a plurality of ions that include precursor ions. The ionisation process and/or the nature of the sample may mean that first fragment ions and/or other ions are also produced.

The precursor ions may be separated from the first fragment and/or other ions generated by the ionisation process, e.g. by passing the ions generated by the ionisation process to one or more separation and/or filtering devices.

At least some of the precursor ions may then be fragmented or reacted so as to produce second fragment ions, e.g. by passing ions that emerge from the one or more separation and/or filtering devices to a fragmentation, reaction or collision device. Ions that emerge from the fragmentation, reaction or collision device may then be analysed.

It will be appreciated that the methods according to various embodiments allow the first fragment and/or other ions that are generated upstream of the one or more separation and/or filtering devices to be distinguished from the second fragment ions that are generated downstream of the one or more separation and/or filtering devices, which could otherwise interfere with one another. The first fragment or other ions that are generated upstream of the one or more separation and/or filtering devices may be rejected, attenuated or otherwise removed from consideration, e.g. such that one or more data sets that do not contain peaks relating to the first fragment or other ions (or that contain fewer or reduced ion peaks corresponding to first fragment or other ions than would otherwise be present) may be produced.

The sample may be classified and/or identified using the so-produced data set(s), i.e. based on the analysis of the second fragment ions optionally together with precursor ions (but without first fragment and/or other ions), e.g. using one or more classification and/or identification algorithms.

As will be explained in more detail below, the Applicants have found that the methods according to various embodiments can reduce the complexity of the one or more data sets that are used for the classification and/or identification, can reduce or remove peaks relating to isobaric species or closely spaced peaks that cannot be resolved from the one or more data sets, and can increase the reproducibility of the one or more data sets, thereby improving the performance of the classification and/or identification algorithms and increasing the likelihood of classifying or identifying the analyte and/or increasing confidence in a classification or identification.

It will be appreciated, therefore, that various embodiments provide an improved method of mass and/or ion mobility spectrometry.

Ionising the analyte may comprise ionising the analyte using a direct analysis ion source.

Ionising the analyte may comprise ionising the analyte using the Rapid Evaporative Ionisation Mass Spectrometry ("REIMS") technique.

Ionising the analyte may comprise ionising the analyte using the Desorption Electrospray Ionisation ("DESI") technique.

The sample may be ionised in its native, unmodified and/or untreated state.

The analyte may comprise one or more lipids.

The analyte may comprise one or more sugars, hydrocarbons, proteins and/or peptides.

Separating precursor ions from first fragment and/or other ions may comprise separating ions according to their ion mobility.

Separating precursor ions from first fragment and/or other ions may comprise filtering ions according to their mass to charge ratio.

Analysing at least some ions that emerge from the fragmentation, reaction or collision device may comprise analysing at least some of the second fragment ions.

Analysing at least some ions that emerge from the fragmentation, reaction or collision device may comprise analysing at least some of the precursor ions.

Analysing at least some ions may comprise mass analysing at least some of the ions that emerge from the fragmentation, reaction or collision device and/or ions derived from at least some of the ions that emerge from the fragmentation, reaction or collision device.

Analysing at least some ions may comprise:

analysing at least some ions so as to produce one or more data sets;

wherein the one or more data sets may comprise data relating to the second fragment ions, without comprising data relating to the first fragment and/or other ions or comprising relatively reduced data relating to the first fragment and/or other ions.

Classifying and/or identifying the sample based on the analysis of the second fragment ions may comprise classifying and/or identifying the sample based on the one or more data sets.

The method may comprise preventing some or all of the first fragment and/or other ions or ions derived from the first fragment and/or other ions from being analysed.

The method may comprise:

analysing at least some of the first fragment and/or other ions or ions derived from the first fragment and/or other ions so as to produce one or more data sets; and removing or attenuating ion peaks corresponding to the first fragment and/or other ions or ions derived from the first fragment and/or other ions from the one or more data sets.

The method may comprise altering the proportion of ions that are fragmented or reacted by the fragmentation, reaction or collision device.

The method may comprise:

operating the collision, reaction or fragmentation device in a fragmentation or reaction mode of operation for a first period of time, and then operating the collision, reaction or fragmentation device in a non-fragmenting or non-reacting mode of operation or a mode of operation in which substantially fewer ions are fragmented or reacted, for a second period of time.

According to an aspect there is provided a method of mass and/or ion mobility spectrometry comprising:

ionising analyte from a sample using a direct analysis ion source so as to generate a plurality of ions;

separating precursor ions from first fragment and/or other ions of the plurality of ions;

fragmenting or reacting at least some of the precursor ions using a fragmentation, reaction or collision device so as to generate second fragment ions;

analysing at least some ions that emerge from the fragmentation, reaction or collision device so as to produce one or more data sets comprising data relating to the second fragment ions without data relating to the first fragment and/or other ions; and classifying and/or identifying the sample based on the one or more data sets.

According to an aspect there is provided a mass and/or ion mobility spectrometer comprising:

an ion source configured to ionise analyte from a sample so as to generate a plurality of ions;

a separation and/or filtering device configured to separate precursor ions from first fragment and/or other ions of the plurality of ions;

a fragmentation, reaction or collision device configured to fragment or react at least some of the precursor ions so as to generate second fragment ions; and an analyser configured to analyse at least some ions that emerge from the fragmentation, reaction or collision device;

wherein the spectrometer is configured to classify and/or identify the sample based on the analysis of the second fragment ions.

The ion source may comprise a direct analysis ion source.

The ion source may comprise a Rapid Evaporative Ionisation Mass Spectrometry ("REIMS") ion source.

The ion source may comprise a Desorption Electrospray Ionisation ("DESI") ion source.

The sample may be provided in its native, unmodified and/or untreated state.

The analyte may comprise one or more lipids.

The analyte may comprise one or more sugars, hydrocarbons, proteins and/or peptides.

The separation and/or filtering device may comprise an ion mobility separator.

The separation and/or filtering device may comprise a mass filter.

The spectrometer and/or the analyser may be configured to analyse at least some of the second fragment ions.

The spectrometer and/or the analyser may be configured to analyse at least some of the precursor ions.

The analyser may comprise a mass analyser.

The spectrometer may be configured to analyse at least some ions so as to produce one or more data sets.

The one or more data sets may comprise data relating to the second fragment ions, without comprising data relating to the first fragment and/or other ions or comprising relatively reduced data relating to the first fragment and/or other ions.

The spectrometer may be configured to classify and/or identify the sample based on the one or more data sets.

The spectrometer may be configured to prevent some or all of the first fragment and/or other ions or ions derived from the first fragment and/or other ions from being analysed by the analyser.

The analyser may be configured to analyse at least some of the first fragment and/or other ions or ions derived from the first fragment and/or other ions so as to produce one or more data sets; and the spectrometer may be configured to remove or attenuate ion peaks corresponding to the first fragment and/or other ions or ions derived from the first fragment and/or other ions from the one or more data sets.

The spectrometer may be configured to alter the proportion of ions that are fragmented or reacted by the fragmentation, reaction or collision device.

The spectrometer may be configured to operate the collision, reaction or fragmentation device in a fragmentation or reaction mode of operation for a first period of time, and then operate the collision, reaction or fragmentation device in a non-fragmenting or non-reacting mode of operation or a mode of operation in which substantially fewer ions are fragmented or reacted, for a second period of time.

According to an aspect, there is provided a method of mass and/or ion mobility spectrometry comprising:

ionising analyte from a sample so as to generate a plurality of ions;

separating lipid precursor ions from first lipid fragment and/or other ions of the plurality of ions;

fragmenting or reacting at least some of the lipid precursor ions using a fragmentation, reaction or collision device so as to generate second lipid fragment ions;

analysing at least some ions that emerge from the fragmentation, reaction or collision device; and classifying and/or identifying the sample based on the analysis of the second lipid fragment ions.

Various embodiments are directed to methods of mass and/or ion mobility spectrometry in which analyte from a biological sample is ionised so as to generate a plurality of ions that include lipid precursor ions. The ionisation process and/or the nature of the sample may mean that first lipid fragment ions and/or other ions are also produced.

The lipid precursor ions may be separated from the first lipid fragment and/or other ions generated by the ionisation process, e.g. by passing the ions generated by the ionisation process to one or more separation and/or filtering devices.

At least some of the lipid precursor ions may then be fragmented or reacted so as to produce second lipid fragment ions, e.g. by passing ions that emerge from the one or more separation and/or filtering devices to a fragmentation, reaction or collision device. Ions that emerge from the fragmentation, reaction or collision device may then be analysed.

It will be appreciated that the methods according to various embodiments allow the first lipid fragment and/or other ions that are generated upstream of the one or more separation and/or filtering devices to be distinguished from the second lipid fragment ions that are generated downstream of the one or more separation and/or filtering devices, which could otherwise interfere with one another. The first fragment or other ions that are generated upstream of the one or more separation and/or filtering devices may be rejected, attenuated or otherwise removed from consideration, e.g. such that one or more data sets that do not contain peaks relating to the first fragment or other ions (or that contain fewer or reduced ion peaks corresponding to first fragment or other ions than would otherwise be present) may be produced.

The sample may be classified and/or identified using the so-produced data set(s), i.e. based on the analysis of the second lipid fragment ions optionally together with lipid precursor ions (but without first lipid fragment and/or other ions), e.g. using one or more classification and/or identification algorithms.

As will be explained in more detail below, the Applicants have found that the methods according to various embodiments can reduce the complexity of the one or more data sets that are used for the classification and/or identification, can reduce or remove peaks relating to isobaric species or closely spaced peaks that cannot be resolved from the one or more data sets, and can increase the reproducibility of the one or more data sets, thereby improving the performance of the classification and/or identification algorithms and increasing the likelihood of classifying or identifying the analyte and/or increasing confidence in a classification or identification.

It will be appreciated, therefore, that various embodiments provide an improved method of mass and/or ion mobility spectrometry.

Ionising the analyte may comprise ionising the analyte using the Rapid Evaporative Ionisation Mass Spectrometry ("REIMS") technique.

Separating lipid precursor ions from first lipid fragment and/or other ions may comprise separating ions according to their ion mobility.

Separating lipid precursor ions from first lipid fragment and/or other ions may comprise filtering ions according to their mass to charge ratio.

Analysing at least some ions that emerge from the fragmentation, reaction or collision device may comprise analysing at least some of the second lipid fragment ions.

Analysing at least some ions that emerge from the fragmentation, reaction or collision device may comprise analysing at least some of the lipid precursor ions.

Analysing at least some ions may comprise mass analysing at least some of the ions that emerge from the fragmentation, reaction or collision device and/or ions derived from at least some of the ions that emerge from the fragmentation, reaction or collision device.

The method may comprise preventing some or all of the first fragment and/or other ions or ions derived from the first fragment and/or other ions from being analysed.

The method may comprise:
analysing at least some of the first fragment and/or other ions or ions derived from the first fragment and/or other ions so as to produce one or more data sets; and
removing or attenuating ion peaks corresponding to the first fragment and/or other ions or ions derived from the first fragment and/or other ions from the one or more data sets.

The method may comprise altering the proportion of ions that are fragmented or reacted by the fragmentation, reaction or collision device.

According to an aspect, there is provided a mass and/or ion mobility spectrometer comprising:
an ion source configured to ionise analyte from a sample so as to generate a plurality of ions;
a separation and/or filtering device configured to separate lipid precursor ions from first lipid fragment and/or other ions of the plurality of ions;
a fragmentation, reaction or collision device configured to fragment or react at least some of the lipid precursor ions so as to generate second lipid fragment ions; and
an analyser configured to analyse at least some ions that emerge from the fragmentation, reaction or collision device;
wherein the spectrometer is configured to classify and/or identify the sample based on analysis of the second lipid fragment ions.

The ion source may comprise a Rapid Evaporative Ionisation Mass Spectrometry ("REIMS") ion source.

The separation and/or filtering device may comprise an ion mobility separator.

The separation and/or filtering device may comprise a mass filter.

The spectrometer and/or the analyser may be configured to analyse at least some of the second lipid fragment ions.

The spectrometer and/or the analyser may be configured to analyse at least some of the lipid precursor ions.

The analyser may comprise a mass analyser.

The spectrometer may be configured to prevent some or all of the first fragment and/or other ions or ions derived from the first fragment and/or other ions from being analysed by the analyser.

The analyser may be configured to analyse at least some of the first fragment and/or other ions or ions derived from the first fragment and/or other ions so as to produce one or more data sets; and
the spectrometer may be configured to remove or attenuate ion peaks corresponding to the first fragment and/or other ions or ions derived from the first fragment and/or other ions from the one or more data sets.

The spectrometer may be configured to alter the proportion of ions that are fragmented or reacted by the fragmentation, reaction or collision device.

According to an aspect, there is provided a method of mass spectrometry comprising:
providing a direct analysis ion source followed by a separator or filter which is in turn followed by a collision cell followed by a mass analyser;
for some proportion of the acquisition time, operating the collision cell in a high energy mode to generate low mass lipid fragments, optionally retaining some proportion of intact lipid precursor species; and configuring the separator or filter and mass analyser to allow (data pertaining to) fragment ions generated downstream of the separator or filter to be distinguished from those generated upstream of the separator or filter.

The method may improve the performance of classification or identification algorithms.

The spectrometer may comprise one or more ion guides.

The spectrometer may comprise one or more ion traps or one or more ion trapping regions.

The spectrometer may comprise one or more energy analysers or electrostatic energy analysers.

The spectrometer may comprise one or more ion detectors.

The spectrometer may comprise a device or ion gate for pulsing ions; and/or a device for converting a substantially continuous ion beam into a pulsed ion beam.

The spectrometer may comprise a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser.

The spectrometer may comprise a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The spectrometer may comprise a device arranged and adapted to supply an AC or RF voltage to the electrodes. The AC or RF voltage optionally has an amplitude selected from the group consisting of: (i) about <50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) > about 500 V peak to peak.

The AC or RF voltage may have a frequency selected from the group consisting of: (i)< about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (xxv) > about 10.0 MHz.

The ion guide may be maintained at a pressure selected from the group consisting of: (i) < about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar; and (ix) > about 1000 mbar.

Analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

Optionally, in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) C60 vapour or atoms; and (viii) magnesium vapour or atoms.

The multiply charged analyte cations or positively charged ions may comprise peptides, polypeptides, proteins or biomolecules.

Optionally, in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

The process of Electron Transfer Dissociation fragmentation may comprise interacting analyte ions with reagent ions, wherein the reagent ions comprise dicyanobenzene, 4-nitrotoluene or azulene.

The spectrometer may be operated in various modes of operation including a mass spectrometry ("MS") mode of operation; a tandem mass spectrometry ("MS/MS") mode of operation; a mode of operation in which parent or precursor ions are alternatively fragmented or reacted so as to produce fragment or product ions, and not fragmented or reacted or fragmented or reacted to a lesser degree; a Multiple Reaction Monitoring ("MRM") mode of operation; a Data Dependent Analysis ("DDA") mode of operation; a Data Independent Analysis ("DIA") mode of operation a Quantification mode of operation or an Ion Mobility Spectrometry ("IMS") mode of operation.

BRIEF DESCRIPTION OF THE DRAWINGS

Various embodiments will now be described, by way of example only, and with reference to the accompanying drawings in which:

FIG. 5 shows fragmentation patterns the lipid ions PE(13: 0/18:1(9Z)) and PE(14:0/17:1(9Z))

DETAILED DESCRIPTION

Figure 1:
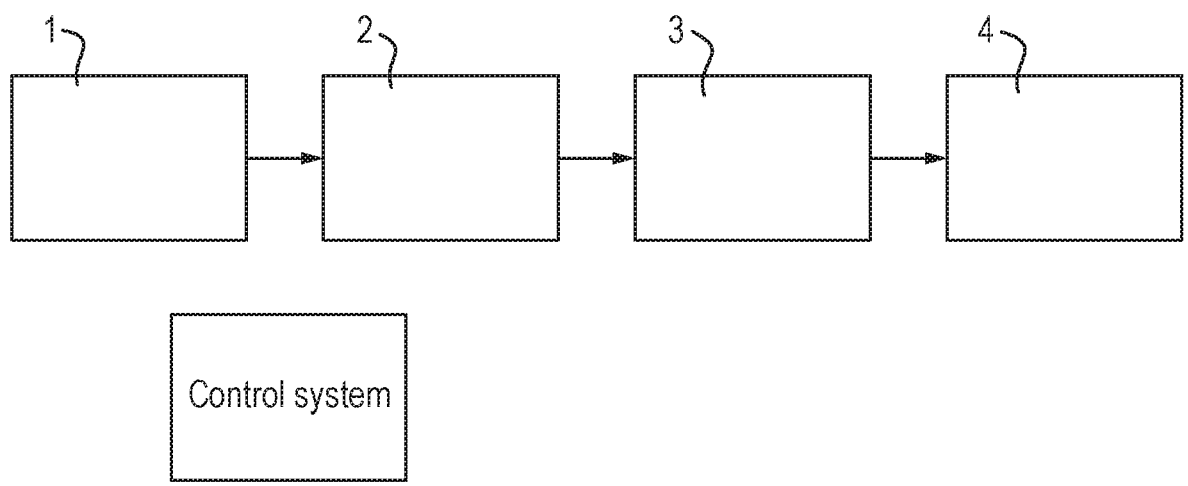
FIG. 1 shows schematically a mass and/or ion mobility spectrometer in accordance with various embodiments.

Various embodiments are directed to methods of mass and/or ion mobility spectrometry in which analyte from a biological sample is ionised so as to generate ions.

The Applicants have found that for many types of biological sample, including, for example, human and animal tissues, food, and microbe cultures, analysis of the lipid profile, e.g. in negative ion mode, provides information that allows the sample to be more easily discriminated from other types of sample, i.e. more easily classified and/or identified.

Ion peaks observed in mass spectra with relatively high mass to charge ratios are often more reproducible than those observed with lower mass to charge ratios, and so subjecting only the relatively high mass to charge ratio ion peaks to classification and/or identification algorithms can improve the performance of the algorithms in classifying and/or identifying the analyte.

In this regard, the Applicants have recognised that many of the less reproducible ion peaks observed in the low mass to charge ratio ("m/z") range may comprise fragment ions of the ions observed in the high mass to charge ratio ("m/z") range. In particular, the ionisation process and/or the nature of the sample may mean that lipid precursor ions (e.g. which may consist largely of phospholipids) having relatively high mass to charge ratios are produced together with first lipid fragment ions and/or other ions having relatively low mass to charge ratios. For example, some of the ion peaks observed in the low mass to charge ratio ("m/z") range may result from fatty acid fragments of the relatively high mass to charge ratio lipid precursor (e.g. phospholipid) ions. In addition, some of the low mass to charge ratio ion peaks may arise from fatty acids present in the sample.

Therefore, the performance of classification and/or identification algorithms can be improved by rejecting or removing relatively low mass to charge ratio ions (which may correspond to in-source fragment ions of the lipid precursor (e.g. phospholipid) ions and fatty acid ions) while keeping relatively high mass to charge ratio ions (which may correspond to lipid precursor (e.g. phospholipid) ions).

However, the Applicants have additionally recognised that the relatively high mass to charge ratio lipid precursor (e.g. phospholipid) ions produced from biological samples may comprise isobaric lipid ions and/or lipid ions that have mass to charge ratios that cannot be differentiated (resolved) (e.g. differing by <4 Da). These species may have overlapping isotope distributions, and it may be difficult, time consuming or even impossible in practice to separate their contributions to the spectra.

In this regard, fragmentation or reaction of these species, e.g. so as to produce second fragment ions, can provide orthogonal information that is useful for classification, and can therefore improve the performance of classification and/or identification algorithms. Therefore, according to various embodiments, at least some of the ions generated by the ion source, e.g. including at least some of the precursor ions, are fragmented or reacted using a fragmentation, reaction or collision cell.

However, the Applicants have also recognised that fragmentation or reaction of the lipid precursor (e.g. phospholipid) ions may result in fragment ions that are the same as and/or have similar or overlapping mass to charge ratios as the relatively low mass to charge ratio first fragment or other (e.g. fatty acid) ions that are produced as part of the ionisation process or otherwise.

Therefore, according to various embodiments, a separation and/or filtering device is provided downstream of the ion source (and upstream of the collision, reaction or fragmentation device), and the spectrometer is configured to separate lipid precursor ions from first lipid fragment and/or other ions of the plurality of ions.

The separation and/or filtering device may comprise, for example, an ion mobility separation device which may be configured to separate ions according to their ion mobility. The lipid precursor (e.g. phospholipid) ions may have larger ion mobility values (e.g. larger collision cross sections or interaction cross sections) than the first lipid fragment and/or other ions, and so the precursor ions may be separated from the first fragment and/or other ions on this basis.

Additionally or alternatively, the separation and/or filtering device may be configured to filter ions according to their mass to charge ratio. The lipid precursor (e.g. phospholipid) ions may have larger mass to charge ratios than the first lipid fragment and/or other ions, and so the precursor ions may be separated from the first fragment and/or other ions on this basis.

Additionally or alternatively, separating the lipid precursor ions from the first lipid fragment and/or other ions may comprise differentially encoding the lipid precursor ions and the first lipid fragment and/or other ions. The step of encoding may comprise separating the ions according to their ion mobility or some other separation, and/or may include separating, modulating and recombining the ions. In these embodiments, where the ions are encoded and recombined, downstream signal processing may be used to partition the fragment ion signals into contributions from the first and second fragment ions.

The separated first fragment and/or other ions may be rejected, attenuated or otherwise prevented from being analysed. Alternatively, at least some of the separated first fragment and/or other ions (or ions derived from these ions) may be analysed (e.g. together with the second fragment ions and optionally some of the precursor ions), and then corresponding ion peaks may be removed from the resulting data set(s).

In this way, the first fragment and/or other ions generated upstream of the separation and/or filtering device can effectively be distinguished from the second fragment ions generated downstream of the separation and/or filtering device.

The spectrometer may produce one or more data sets comprising ion peaks relating to second fragment ions generated downstream of the separation and/or filtering device, i.e. fragment ions produced by the fragmentation, collision or reaction cell (and optionally including ion peaks relating to precursor ions), but not including (or having relatively reduced) less reproducible ion peaks relating to first fragment and/or other ions generated upstream of the separation and/or filtering device, i.e. fragment and/or other ions produced by the ionisation process.

Such data sets may be relatively less complex, may include fewer peaks relating to isobaric species or fewer closely spaced peaks that cannot be resolved, and may have relatively increased reproducibility, thereby increasing the performance of classification and/or identification algorithms that may be applied to the data sets.

The Applicants have furthermore recognised that while the techniques described herein are particularly useful for the analysis of lipids, they can also be used in the analysis of other compound classes such as for example sugars, glycans, proteins and peptides, hydrocarbons, crude oil etc.

In particular, the Applicants have found that sugars can suffer from the same kind of isomerism as described herein with respect to lipids, e.g. with structural and stereoisomers having the same exact mass (same elemental composition) but different fragmentation patterns. As such, the techniques described herein with respect to lipids can be used in the same way for other compounds classes to allow a more accurate classification, i.e. due to the enhanced or increased amount of available data.

For example, the monosaccharides Fructose, Psicose, Sorbose and Tagatose can have the same exact mass but different structures. The fragmentation patterns (i.e. MSMS data) can be used to better classify the compound rather than using non-fragmented data (i.e. MS data). According to various embodiments, the classification can be further improved in the manner described above because for complex mixtures the information content in the mixed spectra is more indicative of the composition of the sample. Furthermore, for these samples, noise in the fragmentation patterns might normally preclude the use of known classifiers, whereas various embodiments result in the fragmentation being more reproducible to the extent that known classifiers may be usable.

In addition, more complex sugars, glycans and oligosaccharides are made up of a combination of simpler sugars, and exhibit the same problems as described herein with respect to lipids, i.e. with low mass to charge ratio ions having low reproducibility. Moreover, these problems can be addressed in accordance with various embodiments in the same way as is described herein with respect to lipids.

Similar cases occur in other complex compounds such as proteins and peptides, hydrocarbons, crude oil etc. The process of separating ions, fragmenting (at least some) ions, analysing and classifying as described herein can provide a more accurate and reproducible classification (fingerprint) for these compounds.

Thus according to various embodiments, the sample may comprise one or more sugars, hydrocarbons, proteins and/or peptides, e.g. wherein the sample is analysed directly in the manner described herein.

FIG. 1 shows a mass and/or ion mobility spectrometer in accordance with various embodiments. The mass and/or ion mobility spectrometer comprises an ion source 1, a separation and/or filtering device 2 that may be arranged downstream of the ion source 1, a collision, reaction or fragmentation device 3 that may be arranged downstream of the separation and/or filtering device 2, and an analyser 4 that may be arranged downstream of the collision, reaction or fragmentation device 3.

As shown in FIG. 1, according to various embodiments, a control system may be provided. The control system may be configured to control the operation of the spectrometer, e.g. in the manner of the various embodiments described herein. The control system may comprise suitable control circuitry that is configured to cause the spectrometer to operate in the manner of the various embodiments described herein. The control system may also comprise suitable processing circuitry configured to perform any one or more or all of the necessary processing and/or post-processing operations in respect of the various embodiments described herein.

The ion source 1 may be configured to ionise analyte. The analyte may comprise any suitable analyte, e.g. from a biological sample or otherwise. The sample may be provided in its native or unmodified state.

According to various embodiments, the sample comprises biological (human or animal) tissue, a food culture, a microbe culture, biological matter, a bacterial colony, and/or a fungal colony. According to various embodiments, the analyte comprises lipids.

According to various other embodiments, the analyte may comprise one or more sugars, one or more proteins and/or peptides, one or more hydrocarbons, crude oil etc.

The ion source 1 may comprise any suitable ion source. The ion source may be an ambient ionisation or direct analysis ion source. Ambient ionisation or direct analysis ion sources are capable of generating gas-phase ions directly from native (i.e. untreated or unmodified) samples. A particular benefit of ambient or direct ionisation techniques is that they do not require any prior sample preparation.

The ion source 1 may be configured to ionise analyte so as to generate ions, e.g. precursor ions. The ion source may also generate first fragment and/or other ions, e.g. sample, pre- or in-source fragment ions. For example, the ion source 1 may produce (e.g. lipid) precursor ions (e.g. consisting largely of phospholipids) that may have relatively high mass to charge ratios, together with first (e.g. lipid) fragment ions and/or other ions, that may have relatively low mass to charge ratios, e.g. including fatty acid fragment ions of the lipid precursor (e.g. phospholipid) ions and/or other fatty acid ions.

According to various embodiments, the ion source comprises a Rapid Evaporative Ionisation Mass Spectrometry ("REIMS") ion source.

Rapid Evaporative Ionisation Mass Spectrometry ("REIMS") may be used for direct analysis of a wide range of samples including (among many others) human and animal tissues, food and microbe cultures.

In the REIMS technique, an electric current is used to generate an aerosol from a sample. Some of the resulting aerosol is passed into the source of a mass and/or ion mobility spectrometer wherein it collides with a heated impact surface. Ions are generated on or near the impact surface and these are transmitted onward through the spectrometer, so as to generate spectra that are characteristic of the type of sample being ionised. Models or libraries created using these spectra can be used for identification of the same sample types.

Figure 2:
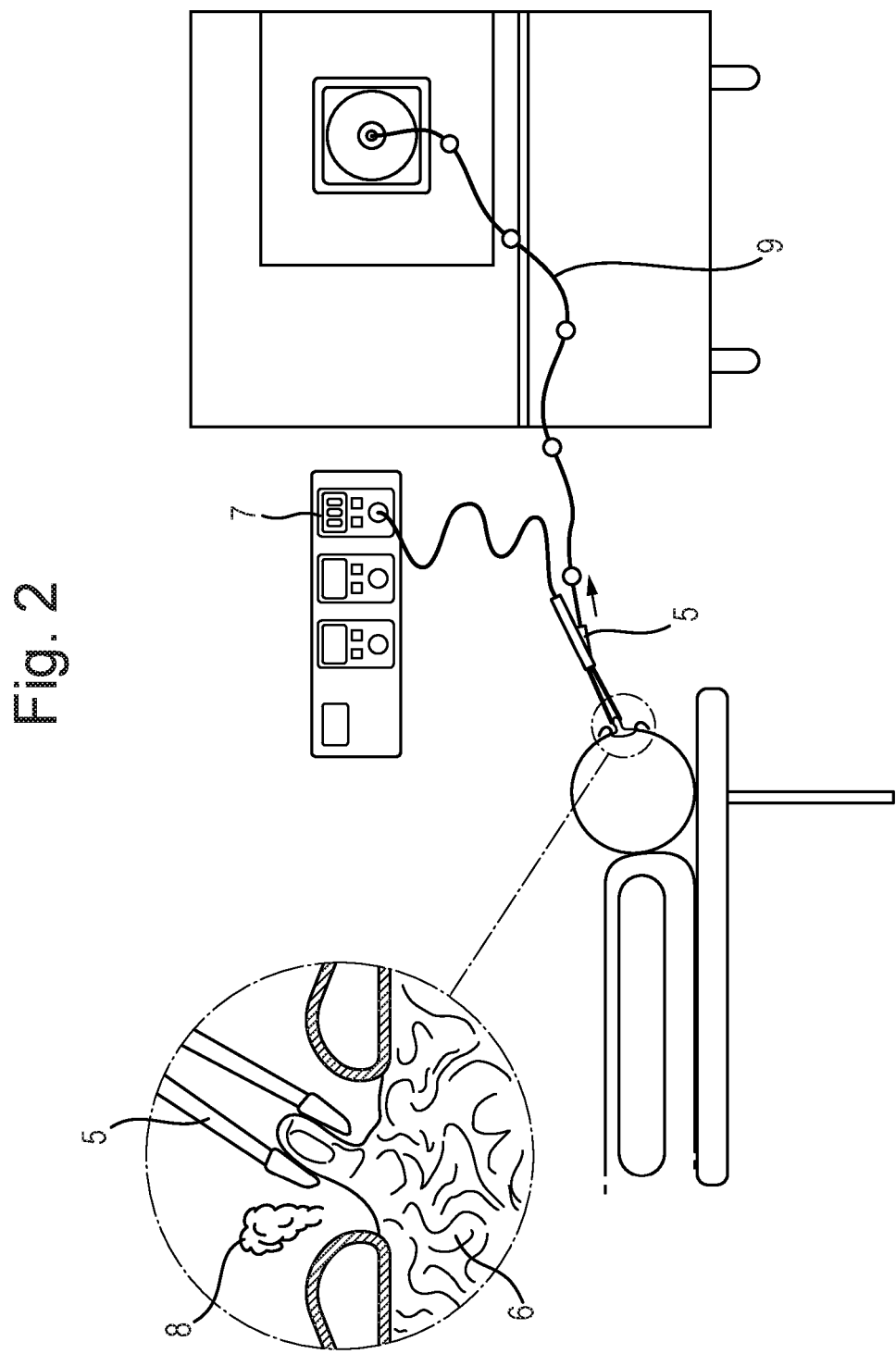
FIG. 2 illustrates schematically the Rapid Evaporative Ionisation Mass Spectrometry ("REIMS") technique according to various embodiments.

FIG. 2 illustrates the Rapid Evaporative Ionisation Mass Spectrometry ("REIMS") technique according to various embodiments.

FIG. 2 illustrates a method of rapid evaporative ionisation mass spectrometry ("REIMS") wherein bipolar forceps 5 may be brought into contact with in vivo tissue 6 of a patient. Other arrangements would be possible, such as the use of a surgical diathermy device in place of the bipolar forceps 5. The technique may be applied to other (biological) samples such as human tissue, animal tissue, food cultures, microbe cultures, biological matter, bacterial colonies, fungal colonies, etc.

An RF voltage from an RF voltage generator 7 may be applied to the bipolar forceps (electrodes) 5 which causes localised Joule or diathermy heating of the tissue 6 or sample. As a result, an aerosol or surgical plume 8 is generated. The aerosol or surgical plume 8 may then be captured or otherwise aspirated through an irrigation port of the bipolar forceps 5. The irrigation port of the bipolar forceps 5 may therefore be reutilised as an aspiration port. The aerosol or surgical plume 8 may then be passed from the irrigation (aspiration) port of the bipolar forceps 5 to tubing 9. The tubing 9 is arranged to transfer the aerosol or surgical plume 8 to an atmospheric pressure interface of a mass and/or ion mobility spectrometer.

According to various embodiments a matrix comprising an organic solvent such as isopropanol may be added to the aerosol or surgical plume 8 at the atmospheric pressure interface. The mixture of aerosol and organic solvent may then be arranged to impact upon a collision surface within a vacuum chamber of the mass and/or ion mobility spectrometer. The collision surface may be heated. The aerosol may be caused to ionise upon impacting the collision surface resulting in the generation of analyte ions. The ionisation efficiency of generating the analyte ions may be improved by the addition of the organic solvent. However, the addition of an organic solvent is not essential.

Analyte ions which are generated by causing the aerosol, smoke or vapour 8 to impact upon the collision surface may then be passed through subsequent stages of the mass and/or ion mobility spectrometer and subjected to separation and/or filtering in separation and/or filtering device 2, fragmentation or reaction in collision, reaction or fragmentation device 3, and analysis in analyser 4.

Figure 3:
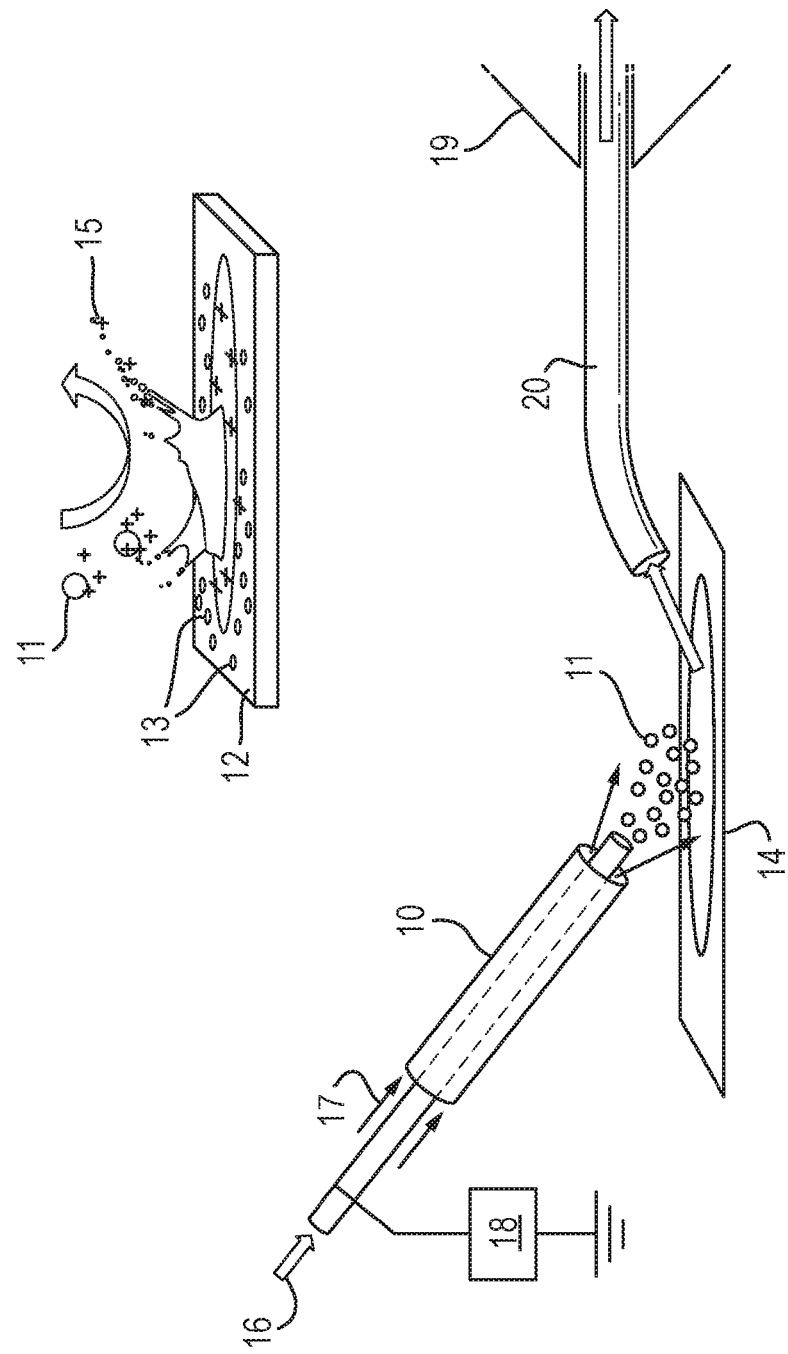
FIG. 3 illustrates schematically the Desorption Electrospray Ionisation ("DESI") technique according to various embodiments.

According to various other embodiments, the ion source may comprise a Desorption ElectroSpray Ionisation ("DESI") ion source. FIG. 3 illustrates the desorption electrospray ionisation ("DESI") technique according to various embodiments.

As shown in FIG. 3, the desorption electrospray ionisation ("DESI") technique is an ambient ionisation method that involves directing a spray of (primary) electrically charged droplets 11 onto a surface 12 with analyte 13 present on the surface 12 and/or directly onto a surface of a sample 14. The electrospray mist is pneumatically directed at the sample by a sprayer 10 where subsequent ejected (e.g. splashed) (secondary) droplets 15 carry desorbed ionised analytes (e.g. desorbed lipid ions).

The sprayer 10 may be supplied with a solvent 16, nebulising gas 17 such as nitrogen, and voltage from a high voltage ("HV") source 18. The solvent 16 may be supplied to a central capillary of the sprayer 10, and the nebulising gas 17 may be supplied to a second capillary that may (at least partially) coaxially surround the central capillary. The arrangement of the capillaries, the flow rate of the solvent 16 and/or the flow rate of the gas 17 may be configured such that solvent droplets are ejected from the sprayer 10. The high voltage may be applied to the central capillary, e.g. such that the ejected solvent droplets 11 are charged.

The charged droplets 11 may be directed at the sample such that subsequent ejected (secondary) droplets 15 carry desorbed analyte ions. The ions travel through air into an atmospheric pressure interface 19 of a mass and/or ion mobility spectrometer or analyser (not shown), e.g. via a transfer capillary 20.

The desorption electrospray ionisation ("DESI") technique allows for ambient ionisation of a trace sample at atmospheric pressure with little sample preparation. The desorption electrospray ionisation ("DESI") technique allows, for example, direct analysis of biological compounds such as lipids, metabolites and peptides in their native state without requiring any advance sample preparation.

It would also be possible to use other ionisation techniques. For example, the ion source may comprise (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a focussed or unfocussed ultrasonic ablation device; (xxii) a microwave resonance device; or (xxiii) a pulsed plasma RF dissection device.

At least some or all of the ions generated by the ion source may be passed to the separation and/or filtering device 2.

The separation and/or filtering device 2 may receive precursor ions generated by the ion source, and also first fragment and/or other ions generated by the ion source or otherwise, and may be configured to separate the precursor ions from the first fragment and/or other ions.

The separation and/or filtering device 2 may comprise a separation device, a filtering device, or a combination of a separation and a filtering device.

The (e.g. lipid) precursor ions may be separated from the first (e.g. lipid) fragment and/or other ions in time and/or in space.

The separation and/or filtering device 2 may be configured to separate ions according to one or more physicochemical properties such as: (i) mass to charge ratio; (ii) ion mobility collision or reaction cross section; and/or (iii) differential ion mobility.

Ions may be separated according to their ion mobility using, for example, an ion mobility separator.

Ions may be separated according to their mass to charge ratio using, for example, a time of flight drift tube or a mass filter.

The mass filter may be selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter.

The mass filter may be operated in a fixed mode of operation, e.g. wherein the mass filter is configured to transmit ions having a particular mass to charge ratio range, or a scanning mode of operation, e.g. wherein the mass filter is configured to scan or vary a mass to charge ratio transmission window. Accordingly, the mass filter may be operated in a 2D tandem mass spectrometry ("2DMSMS") mode of operation, e.g. wherein the mass filter is scanned. This may be done, e.g. to obtain clean fragment spectra, i.e. with improved precursor specificity, to thereby improve the classification and/or identification further.

According to various embodiments, the separation and/or filtering device 2 comprises an ion mobility separation device which may be configured to separate ions according to their ion mobility. The (e.g. lipid) precursor (e.g. phospholipid) ions may have larger ion mobility values (e.g. larger collision cross sections or interaction cross sections) than the first (e.g. lipid) fragment and/or other ions, and so the (e.g. lipid) precursor (e.g. phospholipid) ions may be separated from the first (e.g. lipid) fragment and/or other ions by the ion mobility separation device on this basis.

According to various other embodiments, the separation and/or filtering device may be configured to separate ions according to their mass to charge ratio. The (e.g. lipid) (e.g. phospholipid) precursor ions may have larger mass to charge ratios than the first (e.g. lipid) fragment and/or other ions, and so the (e.g. lipid) precursor (e.g. phospholipid) ions may be separated from the first (e.g. lipid) fragment and/or other ions by the separation and/or filtering device on this basis.

At least some or all of the ions separated by the separation and/or filtering device 2 may be passed to the collision, reaction or fragmentation device 3.

At least some or all of the (e.g. lipid) precursor ions may be passed to the collision, reaction or fragmentation device 3. The first (e.g. lipid) fragment and/or other ions, which are separated from the (e.g. lipid) precursor ions, may also be passed to the collision, reaction or fragmentation device 3, or alternatively may be attenuated or otherwise rejected, i.e. such that first (e.g. lipid) fragment and/or other ions are not passed to the collision, reaction or fragmentation device 3 or such that a relatively reduced number of first (e.g. lipid) fragment and/or other ions are passed to the collision, reaction or fragmentation device 3.

At least some of the (e.g. lipid) precursor ions are fragmented or reacted to produce second (e.g. lipid) fragment ions. The second lipid fragment ions may comprise fatty acid fragment ions of the lipid precursor (e.g. phospholipid) ions, and may have relatively low mass to charge ratios.

The collision, reaction or fragmentation device 3 may comprise any suitable device for fragmenting or reacting ions.

The collision, reaction or fragmentation device 3 may comprise one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) a thermal or temperature source fragmentation device; (xii) an electric field induced fragmentation device; (xiii) a magnetic field induced fragmentation device; (xiv) an enzyme digestion or enzyme degradation fragmentation device; (xv) an ion-ion reaction fragmentation device; (xvi) an ion-molecule reaction fragmentation device; (xvii) an ion-atom reaction fragmentation device; (xviii) an ion-metastable ion reaction fragmentation device; (xix) an ion-metastable molecule reaction fragmentation device; (xx) an ion-metastable atom reaction fragmentation device; (xxi) an ion-ion reaction device for reacting ions to form adduct or product ions; (xxii) an ion-molecule reaction device for reacting ions to form adduct or product ions; (xxiii) an ion-atom reaction device for reacting ions to form adduct or product ions; (xxiv) an ion-metastable ion reaction device for reacting ions to form adduct or product ions; (xxv) an ion-metastable molecule reaction device for reacting ions to form adduct or product ions; (xxvi) an ion-metastable atom reaction device for reacting ions to form adduct or product ions; (xxvii) an Electron Ionisation Dissociation ("EID") fragmentation device; (xxviii) a photo-fragmentation device; and (xxix) a negative electron transfer dissociation ("nETD") fragmentation device.

The collision, reaction or fragmentation device 3 may be operated to fragment or react most or all of the received precursor ions to produce second fragment ions. Alternatively, the collision, reaction or fragmentation device 3 may be operated to fragment or react only a proportion of the received precursor ions, in which case at least some of the precursor ions may emerge from the collision, reaction or fragmentation device 3 (i.e. together with second fragment ions).

The collision, reaction or fragmentation device 3 may be operated substantially continuously in a fragmentation or reaction mode of operation, so as to fragment or react all or some (e.g. fixed) proportion of the received ions.

Alternatively, the proportion of ions that are fragmented or reacted by the fragmentation, reaction or collision device may be altered.

For example, the collision, reaction or fragmentation device 3 may be operated for some period of time in a fragmentation or reaction mode of operation, and may be operated in a non-fragmenting or non-reacting mode of operation, or a mode of operation in which substantially fewer ions are fragmented or reacted, for some other period of time.

Accordingly, the collision, reaction or fragmentation device 3 may be operated in a "High/Low" or "$MS^e$" mode of operation. In these embodiments, the resulting low energy data (e.g. that will not comprise second fragment (e.g. lipid) ions or that will comprise a reduced number of second fragment (e.g. lipid) ions) may be compared with or subtracted from the high energy data (e.g. that will comprise second fragment (e.g. lipid) ions), e.g. so as to associate second (e.g. lipid) fragment ions with their corresponding (e.g. lipid) precursor ions and/or identify the second (e.g. lipid) fragment ions.

Additionally or alternatively, the proportion of ions that are fragmented or reacted by the fragmentation, reaction or collision device may be altered in a stepped and/or continuous manner. For example, the collision energy may be ramped, e.g. within the scan time.

At least some of the ions that emerge from the fragmentation, reaction or collision cell 3, e.g. including second fragment ions and optionally some intact (e.g. lipid) precursor ions, are analysed.

Where the first fragment or other ions are not (completely) rejected or attenuated prior to the fragmentation, reaction or collision device, then these ions and/or ions derived from these ions may be rejected or attenuated after the fragmentation, reaction or collision device, and before being analysed. Alternatively, at least some of these ions may be analysed.

Analysing the ions that emerge from the fragmentation, reaction or collision cell 3 may comprise passing the ions that emerge from the fragmentation, reaction or collision cell 3 to the analyser 4 for analysis. Alternatively, analysing ions that emerge from the fragmentation, reaction or collision cell 3 may comprises passing ions derived from the ions that emerge from the fragmentation, reaction or collision cell 3 to the analyser 4 for analysis.

The analyser 4 may comprise any suitable device for analysing ions. The analyser 4 may comprise, for example, a mass analyser, i.e. an analyser configured to determine the mass to charge ratio of ions.

The mass analyser may be selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser.

It will be appreciated that the methods according to various embodiments allow the first (e.g. lipid) fragment and/or other ions that are generated upstream of the one or more separation and/or filtering devices (i.e. fragment ions generated by the ion source 1, such as sample, pre- or in-source fragment ions (which may comprise fatty acid fragment or other fatty acid ions)) to be distinguished from the second (e.g. lipid) fragment ions that are generated downstream of the one or more separation and/or filtering devices (i.e. fragment ions generated by the collision, reaction or fragmentation device 3).

According to various embodiments, first fragment and/or other ions generated upstream of the separation and/or filtering device 2 (or ions derived from these ions) may be prevented from reaching the analyser 4 or otherwise prevented from being analysed by the analyser 4.

This may be achieved in any suitable manner. For example, where the separation and/or filtering device 2 comprises an ion mobility separator, then ions having ion mobility drift times within a selected range may be rejected, attenuated or otherwise prevented from being analysed. The selected range may comprise, for example, ion mobility drift times below a threshold value. The threshold value may be selected as appropriate.

Where the separation and/or filtering device 2 comprises a mass filter, then ions having mass to charge ratios within a selected range may be rejected, attenuated or otherwise prevented from being analysed. According to various embodiments, a mass selective ion trap may be provided and used to prevent ions within the selected range from being analysed. The selected range may comprise, for example, mass to charge ratios below a threshold value. The threshold value may be selected as appropriate.

According to various other embodiments, at least some or all of the fragment ions generated upstream of the separation and/or filtering device 2 (or ions derived from these ions) may be analysed (together with other ions that emerge from the collision, reaction or fragmentation device 3), e.g. so as to produce one or more first data sets, but may then be distinguished from the second fragment ions generated downstream of the separation and/or filtering device in post-processing.

This may again be achieved in any suitable manner. For example, where the separation and/or filtering device 2 comprises an ion mobility separator, then ions having ion mobility drift times within a selected range may be rejected, attenuated or otherwise removed from the one or more first data sets. The selected range may comprise, for example, ion mobility drift times below a threshold value. The threshold value may be selected as appropriate.

Where the separation and/or filtering device 2 comprises a mass filter, then ions having mass to charge ratios within a selected range may be rejected, attenuated or otherwise removed from the one or more first data sets. The selected range may comprise, for example, mass to charge ratios below a threshold value. The threshold value may be selected as appropriate.

Accordingly, the first fragment or other ions that are generated upstream of the separation and/or filtering device may be rejected, attenuated or otherwise removed from consideration, e.g. such that one or more data sets that do not contain peaks corresponding to the first fragment or other ions (or that contain fewer or reduced ion peaks corresponding to first fragment or other ions than would otherwise be present) may be produced.

The sample may be classified and/or identified using the so-produced data set(s), i.e. based on the analysis of the second (e.g. lipid) fragment ions optionally together with (e.g. lipid) precursor ions (but without first (e.g. lipid) fragment and/or other ions), e.g. using one or more classification and/or identification algorithms. The one or more classification and/or identification algorithms may utilise multivariate statistical analysis.

The Applicants have found that the methods according to various embodiments can reduce the complexity of the one or more data sets, can reduce or remove peaks relating to isobaric species or closely spaced peaks that cannot be resolved from the one or more data sets, and can increase the reproducibility of the one or more data sets, thereby improving the performance of the classification and/or identification algorithms and increasing the likelihood of classifying or identifying the analyte and/or increasing confidence in a classification or identification.

Figure 4:
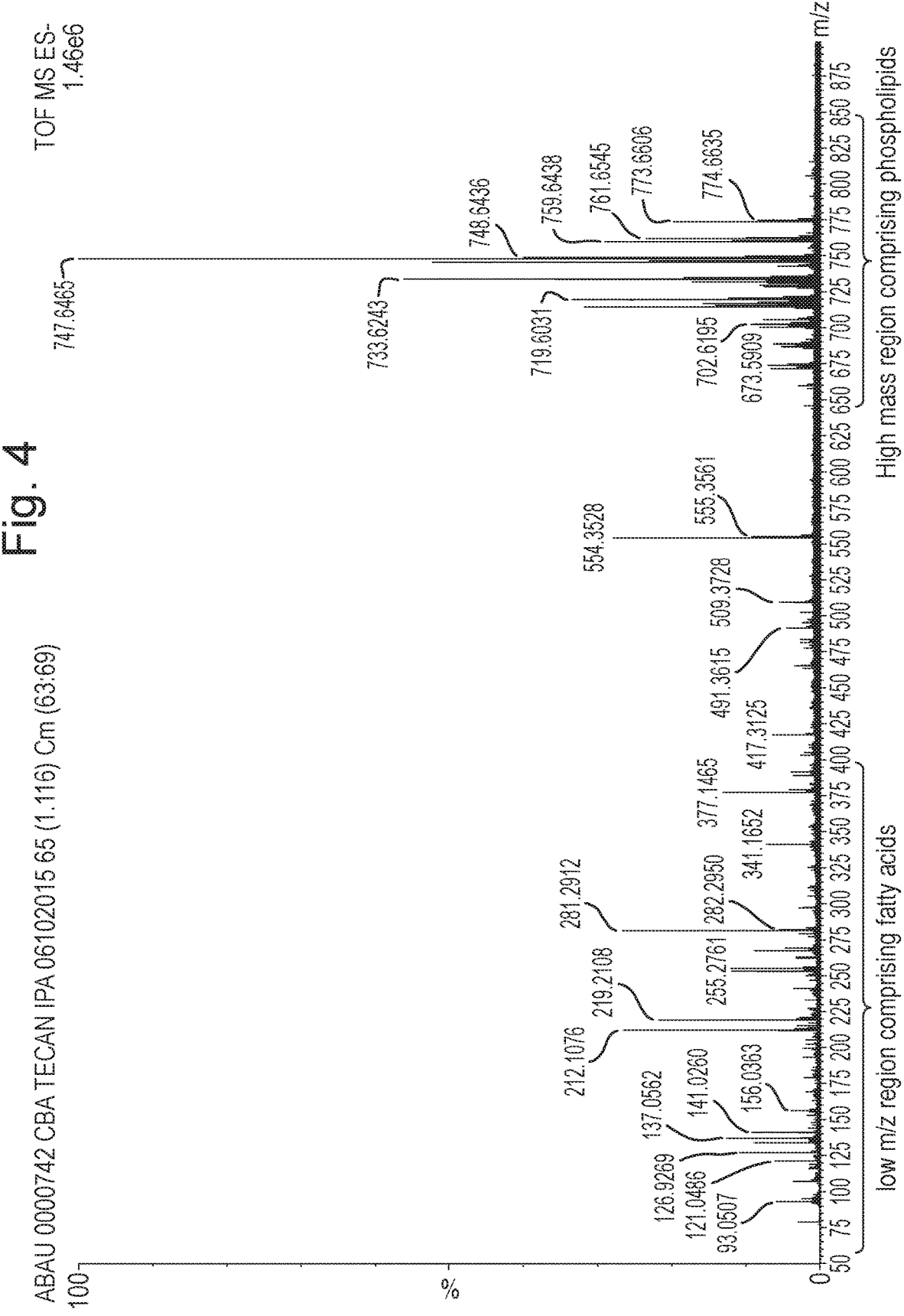
FIG. 4 shows a typical REIMS spectrum from a microbe culture.

FIG. 4 shows a typical mass spectrum from a microbe culture obtained using the REIMS technique.

Although singly charged ion peaks are seen throughout the mass to charge ratio ("m/z") range 50-1000 (and beyond), restricting the mass to charge ratio ("m/z") range to 600-900 (consisting largely of phospholipid ions) typically produces improved classification results, e.g. when using multivariate statistical analysis. This is consistent with the observation described above, that the patterns of peak intensities observed in the higher mass to charge ratio range are typically more reproducible than those seen at lower mass to charge ratios ("m/z") (e.g. m/z 50-400).

As described above, many of the less reproducible peaks observed in the low mass to charge ratio ("m/z") region comprise fragments of species observed in the high mass to charge ratio ("m/z") range. In particular, some of the species observed at low mass to charge ratios ("m/z") are fatty acid fragment ions of the lipid precursor ions. In addition, some of these ion peaks may arise from fatty acids present in the original sample.

However, as also described above, isobaric lipid ions and lipid ions with masses differing by, e.g., <4 Da may be present in the same sample. These species may have overlapping isotope distributions, and it may be difficult, time consuming or even impossible in practice to separate their contributions to the mass spectral data.

For example, as shown in Table 1, an ion peak observed at an exact mass of 674.4766 Da may comprise of one or more of 22 different lipid ions.

TABLE 1

| COMMON NAME | SYSTEMATIC NAME | FORMULA | MASS |
|---|---|---|---|
| PC(10:0/18:1(9Z)) | 1-decanoyl-2-(9Z-octadecenoyl)-sn-qlycero-3-phosphocholine | C36H70NO8P | 675.4839 |
| PC(12:0/16:1(9Z)) | 1-dodecanoyl-2-(9Z-hexadecenoyl)-qlycero-3-phosphocholine | C36H70NO8P | 675.4839 |
| PC(13:0/15:1(9Z)) | 1-tridecanoyl-2-(9Z-pentadecenoyl)-qlycero-3-phosphocholine | C36H70NO8P | 675.4839 |
| PC(14:0/14:1(9Z)) | 1-tetradecanoyl-2-(9Z-tetradecenoyl)-qlycero-3-phosphocholine | C36H70NO8P | 675.4839 |
| PC(14:1(9Z)/14:0) | 1-(9Z-tetradecenoyl)-2-tetradecanoyl-qlycero-3-phosphocholine | C36H70NO8P | 675.4839 |
| PC(15:1(9Z)/13:0) | 1-(9Z-pentadecenoyl)-2-tridecanoyl-qlycero-3-phosphocholine | C36H70NO8P | 675.4839 |
| PC(16:1(9Z)/12:0) | 1-(9Z-hexadecenoyl)-2-dodecanoyl-qlycero-3-phosphocholine | C36H70NO8P | 675.4839 |
| PE(17:0/14:1(9Z)) | 1-heptadecanoyl-2-(9Z-tetradecenoyl)-sn-qlycero-3-phosphoethanolamine | C36H70NO8P | 675.4839 |
| PE(16:1(11Z)/15:0) | 1-(11Z-hexadecenoyl)-2-pentadecanoyl-sn-qlycero-3-phosphoethanolamine | C36H70NO8P | 675.4839 |
| PE(16:1(5Z)/15:0) | 1-(5Z-hexadecenoyl)-2-pentadecanoyl-sn-qlycero-3-phosphoethanolamine | C36H70NO8P | 675.4839 |
| PE(12:0/19:1(9Z)) | 1-dodecanoyl-2-(9Z-nonadecenoyl)-qlycero-3-phosphoethanolamine | C36H70NO8P | 675.4839 |
| PE(13:0/18:1(9Z)) | 1-tridecanoyl-2-(9Z-octadecenoyl)-qlycero-3-phosphoethanolamine | C36H70NO8P | 675.4839 |
| PE(14:0/17:1(9Z)) | 1-tetradecanoyl-2-(9Z-heptadecenoyl)-qlycero-3-phosphoethanolamine | C36H70NO8P | 675.4839 |
| PE(14:1(9Z)/17:0) | 1-(9Z-tetradecenoyl)-2-heptadecanoyl-qlycero-3-phosphoethanolamine | C36H70NO8P | 675.4839 |
| PE(15:1(9Z)/16:0) | 1-(9Z-pentadecenoyl)-2-hexadecanoyl-qlycero-3-phosphoethanolamine | C36H70NO8P | 675.4839 |
| PE(16:0/15:1(9Z)) | 1-hexadecanoyl-2-(9Z-pentadecenoyl)-qlycero-3-phosphoethanolamine | C36H70NO8P | 675.4839 |
| PE(16:1(9Z)/15:0) | 1-(9Z-hexadecenoyl)-2-pentadecanoyl-glycero-3-phosphoethanolamine | C36H70NO8P | 675.4839 |
| PE(17:1(9Z)/14:0) | 1-(9Z-heptadecenoyl)-2-tetradecanoyl-glycero-3-phosphoethanolamine | C36H70NO8P | 675.4839 |
| PE(18:1(9Z)/13:0) | 1-(9Z-octadecenoyl)-2-tridecanoyl-glycero-3-phosphoethanolamine | C36H70NO8P | 675.4839 |
| PE(19:1(9Z)/12:0) | 1-(9Z-nonadecenoyl)-2-dodecanoyl-glycero-3-phosphoethanolamine | C36H70NO8P | 675.4839 |

TABLE 1-continued

| COMMON NAME | SYSTEMATIC NAME | FORMULA | MASS |
|---|---|---|---|
| PE(15:0/16:1(9Z)) | 1-pentadecanoyl-2-(9Z-hexadecenoyl)-glycero-3-phosphoethanolamine | C36H70NO8P | 675.4839 |

Each lipid ion will have a characteristic fragmentation pattern. If, by way of example, the fragmentation patterns of two of the lipid ions PE(13:0/18:1(9Z)) and PE(14:0/17:1(9Z)) are examined (as shown in FIG. 5), it can be seen that significantly more information can be obtained using fragmentation than would otherwise be obtained using the mass spectrometry ("MS") data of FIG. 4 alone.

Therefore, as described above, according to various embodiments, reproducible fragmentation of these species is used to provide orthogonal information that may be used during classification.

This may be achieved by providing a direct analysis ion source, followed by a separator and/or filter, which is in turn followed by a collision cell or fragmentation device, followed by a mass analyser. For some proportion of the acquisition time, the collision cell may be operated in a high energy mode of operation to generate low mass to charge ratio fragment ions, optionally retaining some proportion of intact precursor ions. The separator and/or filter and mass analyser may be configured to allow (data pertaining to) fragment ions generated downstream of the separator and/or filter to be distinguished from those generated upstream of the separator and/or filter.

For example, the separator may be an ion mobility device, and the mass analyser may be a time of flight mass spectrometer. Fatty acid ions and fragment ions of lipids generated upstream of the mobility separator will have relatively low drift times, while intact lipid ions will appear at higher drift times. If the time of flight ("ToF") mass spectrometer is operated on a sufficiently short time scale, then the data corresponding to the upstream fragment ions may be rejected by applying a low drift time cut-off, and highly reproducible fragment information may be generated.

According to various other embodiments, data generated from upstream fragment ions can also be substantially removed by a mass filter such as a quadrupole mass filter operating in RF only mode placed between the ion source and the mass analyser having a low mass cut-off in the gap between the low mass to charge ratio ("m/z") and high mass to charge ratio ("m/z") ranges.

Figure 6:
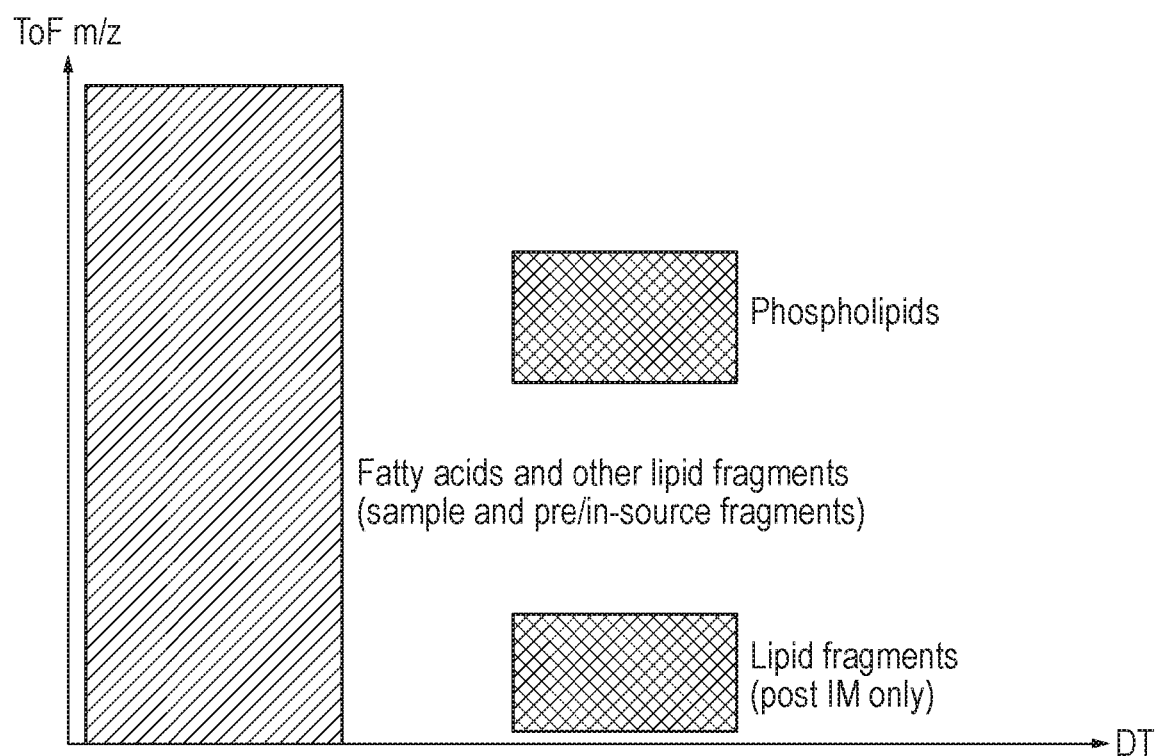
FIG. 6 illustrates schematically how first fragment and/or other ions may be distinguished from second fragment ions according to various embodiments.

FIG. 6 schematically illustrates the use of ion mobility to separate in-source fragment ions from fragment ions produced after the mobility separation. Imposing a low drift time ("DT") cut-off on this data and combining the remaining data can produce highly reproducible phospholipid/fragmentation data. Alternatively, the cut-off may be applied in hardware, e.g. as described above.

It will be appreciated that various embodiments are directed to methods for utilising fragmentation in rapid evaporative ionisation mass spectrometric ("REIMS") analysis of lipids and other compound classes.

Various embodiments are directed to a method of mass spectrometry in which a direct analysis ion source followed by a (downstream) separator or filter is provided, which is in turn followed by a (downstream) reaction or collision cell followed by a (downstream) mass analyser.

According to various embodiments, for some proportion of the acquisition time, the reaction or collision cell is operated in a high energy mode of operation, e.g. so as to generate low mass (e.g. lipid) fragments, while optionally retaining some proportion of intact (e.g. lipid) precursor ions.

According to various embodiments, the separator or filter and mass analyser are configured to allow (data pertaining to) fragment ions generated downstream of the separator or filter to be distinguished from those generated upstream of the separator or filter.

Accordingly, the performance of classification or identification algorithms can be improved.

According to various embodiments, the collision energy may be ramped within the scan time.

According to various embodiments, post-quadrupole methods of fragmentation (e.g. photo-fragmentation, nETD etc.) may be utilised.

According to various embodiments, a trap may be used to obtain a low mass cut-off.

According to various embodiments, any type of mass analyser, including RF and electrostatic traps, may be used.

According to various embodiments, $MS^E$-type acquisition may be performed, e.g. with a selected low mass to charge ratio cut-off. Classification may be performed on composite data.

According to various embodiments, 2D tandem mass spectrometry ("2DMSMS") may be performed to obtain clean fragment spectra with improved precursor specificity.

According to various embodiments, the method may comprise differentially encoding the (e.g. lipid) precursor ions and the first (e.g. lipid) fragment and/or other ions, e.g. instead of or in addition to separating the (e.g. lipid) precursor ions from the first (e.g. lipid) fragment and/or other ions. The step of encoding may comprise separating the ions according to their ion mobility or some other separation, and/or may include separating, modulating and recombining the ions. In these embodiments, where the ions are encoded and recombined, downstream signal processing may be used to partition the fragment ion signals into contributions from the first and second fragment ions.

It will be appreciated that various embodiments provide increased reproducibility in the mass spectra. In addition, more information is provided compared to a "standard" mass spectrometry mode of operation, wherein at each mass to charge ratio ("m/z") value the information content may be a single value of intensity corresponding to multiple species. In contrast, by fragmenting or reacting the precursor ions in accordance with various embodiments, more information is gained as each species produces multiple ions, some of which may be unique and some of which common. The ratios of the common fragment ions may also provide a more unique fingerprint, thereby leading to a clearer separation of classification results.

Although the present invention has been described with reference to preferred embodiments, it will be understood by those skilled in the art that various changes in form and detail may be made without departing from the scope of the invention as set forth in the accompanying claims.

The invention claimed is:

1. A method of mass and/or ion mobility spectrometry comprising:
ionising analyte from a sample so as to generate a plurality of ions, wherein the plurality of ions comprises precursor ions and first fragment ions;
separating the precursor ions from the first fragment ions by separating the plurality of ions according to their mass to charge ratio;
fragmenting or reacting at least some of the precursor ions using a fragmentation, reaction or collision device so as to generate second fragment ions;
analysing at least some ions that emerge from the fragmentation, reaction or collision device, including analysing at least some of the second fragment ions;
selecting a mass to charge ratio threshold value;
preventing some or all of the first fragment ions or ions derived from the first fragment ions from being analysed by preventing ions having mass to charge ratios below the selected threshold value from being analysed; and
classifying and/or identifying the sample based on the analysis of the second fragment ions.

2. A method as claimed in claim 1, wherein ionising the analyte comprises ionising the analyte using a Rapid Evaporative Ionisation Mass Spectrometry ("REIMS") technique.

3. A method as claimed in claim 1, wherein ionising the analyte comprises ionising the analyte using a Desorption Electrospray Ionisation ("DESI") technique.

4. A method as claimed in claim 1, wherein the sample is ionised in its native, unmodified and/or untreated state.

5. A method as claimed in claim 1, wherein the analyte comprises one or more lipids.

6. A method as claimed in claim 1, wherein the analyte comprises one or more sugars, hydrocarbons, proteins and/or peptides.

7. A method as claimed in claim 1, wherein analysing at least some ions that emerge from the fragmentation, reaction or collision device comprises analysing at least some of the precursor ions.

8. A method as claimed in claim 1, wherein analysing at least some ions comprises mass analysing at least some of the ions that emerge from the fragmentation, reaction or collision device and/or ions derived from at least some of the ions that emerge from the fragmentation, reaction or collision device.

9. A method as claimed in claim 1, wherein analysing at least some ions comprises:
analysing at least some ions so as to produce one or more data sets;
wherein the one or more data sets comprise data relating to the second fragment ions, without comprising data relating to the first fragment ions or comprising relatively reduced data relating to the first fragment ions.

10. A method as claimed in claim 9, wherein classifying and/or identifying the sample based on the analysis of the second fragment ions comprises classifying and/or identifying the sample based on the one or more data sets.

11. A method as claimed in claim 1, further comprising altering a proportion of ions that are fragmented or reacted by the fragmentation, reaction or collision device.

12. A method as claimed in claim 11, further comprising:
operating the collision, reaction or fragmentation device in a fragmentation or reaction mode of operation for a first period of time, and then operating the collision, reaction or fragmentation device in a non-fragmenting or non-reacting mode of operation or a mode of operation in which substantially fewer ions are fragmented or reacted, for a second period of time.

13. A method as claimed in claim 1, wherein preventing some or all of the first fragment ions or ions derived from the first fragment ions from being analysed comprises passing some or all of the first fragment ions or ions derived from the first fragment ions to a RF-only quadrupole mass filter having a low mass cut-off corresponding to said mass to charge ratio threshold value.

14. A mass and/or ion mobility spectrometer configured to perform the method of claim 1.

15. A method of mass and/or ion mobility spectrometry comprising:
ionising analyte from a sample so as to generate a plurality of ions, wherein the plurality of ions comprises precursor ions and first fragment ions;
separating the precursor ions from the first fragment ions by separating the ions according to their ion mobility, wherein the ions have different ion mobility drift times;
fragmenting or reacting at least some of the precursor ions using a fragmentation, reaction or collision device so as to generate second fragment ions;
analysing at least some ions that emerge from the fragmentation, reaction or collision device, including analysing at least some of the second fragment ions;
selecting an ion mobility drift time threshold value;
preventing some or all of the first fragment ions or ions derived from the first fragment ions from being analysed by preventing ions having ion mobility drift times below the selected threshold value from being analysed; and
classifying and/or identifying the sample based on the analysis of the second fragment ions.

16. A mass and/or ion mobility spectrometer configured to perform the method of claim 15.

17. A method of mass and/or ion mobility spectrometry comprising:
ionising analyte from a sample so as to generate a plurality of ions, wherein the plurality of ions comprises precursor ions and first fragment ions;
separating the precursor ions from the first fragment ions by separating the ions according to their ion mobility, wherein the ions have different ion mobility drift times, and/or separating the ions according to their mass to charge ratio;
fragmenting or reacting at least some of the precursor ions using a fragmentation, reaction or collision device so as to generate second fragment ions;
analysing at least some ions that emerge from the fragmentation, reaction or collision device, including analysing at least some of the second fragment ions;
selecting an ion mobility drift time threshold value and/or mass to charge ratio threshold value;
removing or attenuating ion peaks corresponding to the first fragment ions or ions derived from the first fragment ions from one or more data sets comprising data relating to the second fragment ions by removing or attenuating ions having ion mobility drift times below the ion mobility drift time threshold value and/or having mass to charge ratios below the selected mass to charge ratio threshold value; and
classifying and/or identifying the sample based on the analysis of the second fragment ions.

18. A mass and/or ion mobility spectrometer configured to perform the method of claim 17.

* * * * *